US012685432B2

(12) United States Patent
Mayer

(10) Patent No.: US 12,685,432 B2
(45) Date of Patent: Jul. 21, 2026

(54) MEASURING DEVICE FOR AN ENDOSCOPE FOR READJUSTING A MAXIMUM LUMINOSITY

(71) Applicant: HOYA CORPORATION, Tokyo (JP)

(72) Inventor: Wolfgang Mayer, Ehingen am Ries (DE)

(73) Assignee: HOYA CORPORATION, Tokyo (JP)

( * ) Notice: Subject to any disclaimer, the term of this patent is extended or adjusted under 35 U.S.C. 154(b) by 303 days.

(21) Appl. No.: 18/684,410

(22) PCT Filed: Aug. 11, 2022

(86) PCT No.: PCT/IB2022/057506
§ 371 (c)(1),
(2) Date: Feb. 16, 2024

(87) PCT Pub. No.: WO2023/021380
PCT Pub. Date: Feb. 23, 2023

(65) Prior Publication Data
US 2024/0349988 A1 Oct. 24, 2024

(30) Foreign Application Priority Data
Aug. 19, 2021 (DE) ..................... 10 2021 121 523.4

(51) Int. Cl.
*A61B 1/00* (2006.01)
*A61B 1/07* (2006.01)

(52) U.S. Cl.
CPC ............ *A61B 1/00057* (2013.01); *A61B 1/07* (2013.01)

(58) Field of Classification Search
CPC ....... A61B 50/13; A61B 1/00057; A61B 1/07; A61B 1/00676; A61B 50/07
See application file for complete search history.

(56) References Cited

U.S. PATENT DOCUMENTS

2003/0107726 A1 6/2003 Hirt et al.
2004/0064018 A1* 4/2004 Dunki-Jacobs ...... A61B 1/0684
600/178

(Continued)

FOREIGN PATENT DOCUMENTS

CN 101452113 A 6/2009
CN 103997945 A 8/2014

(Continued)

OTHER PUBLICATIONS

Notice of Reasons for Refusal issued in Japanese Patent Application No. 2024-504886, dated Oct. 22, 2024, together with an English translation.

(Continued)

*Primary Examiner* — Aaron B Fairchild
(74) *Attorney, Agent, or Firm* — Greenblum & Bernstein, P.L.C.

(57) ABSTRACT

Disclosed herein is an endoscope apparatus comprising a measuring device mountable on an endoscope head of the endoscope apparatus for determining a characteristic parameter of an endoscope lighting of the endoscope apparatus, wherein the endoscope lighting comprises at least one optical element through which light passes, wherein the measuring device comprises a light detection unit adapted to determine the characteristic parameter, wherein the endoscope head comprises a light exit area through which the endoscope lighting outputs a light amount of a light emitted from a light source, the light emitted from the light source having a luminosity up to a preset maximum luminosity, and the characteristic parameter is based on the light amount incident on the light detection unit; and a processing unit adapted to readjust the preset maximum luminosity based on the determined characteristic parameter.

19 Claims, 4 Drawing Sheets

(56) References Cited

U.S. PATENT DOCUMENTS

| | | |
|---|---|---|
| 2009/0147077 A1 | 6/2009 | Tani et al. |
| 2014/0204188 A1 | 7/2014 | Ariyoshi et al. |
| 2014/0246563 A1 | 9/2014 | McCaffrey et al. |
| 2016/0015247 A1 | 1/2016 | Irion et al. |
| 2017/0296041 A1 | 10/2017 | McCaffrey et al. |
| 2018/0042470 A1 | 2/2018 | Tanaka et al. |
| 2019/0029500 A1 | 1/2019 | McCaffrey et al. |
| 2019/0159663 A1 | 5/2019 | Krstajic et al. |
| 2021/0251473 A1 | 8/2021 | McCaffrey et al. |
| 2023/0389786 A1 | 12/2023 | Mayer et al. |

FOREIGN PATENT DOCUMENTS

| | | |
|---|---|---|
| CN | 107405064 A | 11/2017 |
| CN | 109310296 A | 2/2019 |
| JP | H04-307025 A | 10/1992 |
| JP | H07-124107 A | 5/1995 |
| JP | 2003-519790 A | 6/2003 |
| JP | 2004-208781 A | 7/2004 |

OTHER PUBLICATIONS

International Search Report issued in WIPO Patent Application No. PCT/IB2022/057506, dated Nov. 8, 2022.
First Office Action issued in Chinese Patent Application No. 202280047413.8, dated May 13, 2026, together with an English translation.

\* cited by examiner

MEASURING DEVICE FOR AN ENDOSCOPE FOR READJUSTING A MAXIMUM LUMINOSITY

FIELD OF THE DISCLOSURE

The present disclosure relates to an endoscope apparatus having a measuring device in which a maximum luminosity can be readjusted.

TECHNICAL PROBLEM

The light output power, or luminosity, of light emitted at a distal end of an endoscope or endoscope apparatus, can decrease over time, for example due to degradation effects. Examples of degradation effects include the occurrence of fiber breaks in individual optical fibers and increasing fiber connector losses when light is coupled into the optical fibers, assuming an endoscope apparatus with optical fibers is used. Further examples of degradation effects regarding an endoscope head also include a haze or contamination of an existing expanding optics (e.g. an expanding lens) or an existing light exit window. The light exit window may be provided in, for example, a cap that can be plugged onto the endoscope head to cover a light exit opening, or light exit window or light exit area (from which light is emitted via, for example, the expanding optics) and/or a light incidence opening, or light entrance window or light incidence area (for example, for a camera integrated in the endoscope head). As a result, the required light output power at the distal end of the endoscope apparatus for using the endoscope head in, for example, a body cavity of a subject, may not always be available. Replacing the elements affected by degradation is usually time-consuming, material-intensive, and costly.

It is therefore an object of the present disclosure to provide an endoscope apparatus with which such disadvantages can be eliminated.

SOLUTION TO THE PROBLEM

The present disclosure solves the problem described above by means of an endoscope apparatus having a measuring device according to claim 1. Examples thereof are detailed in the dependent claims.

In particular, an endoscope apparatus with a measuring device that is mountable on the endoscope head for determining a characteristic parameter (e.g. characteristic value or characteristic quantity or property) of an endoscope lighting (e.g. a lighting assembly or lighting unit) of the endoscope apparatus is disclosed, having a light detection unit and a processing unit. The endoscope lighting has at least one optical element through which the light passes.

The mounting of the measuring device can be implemented in different ways, for example (but not limited to) by placing on or plugging on the measuring device, by means of an external holding device, such as a clamp or bracket, by a plug-and-turn lock such as a bayonet lock, and/or by means of a magnetic holding device.

For communication with the endoscope apparatus, the measuring device can be connected to the endoscope apparatus wirelessly or by wire/cable, directly or indirectly via a communication interface. The processing unit may be provided in the endoscope apparatus, the measuring device, or an external device connected wirelessly or by wire/cable to at least the endoscope apparatus, the measuring device, or the communication interface.

The light detection unit is adapted, or configured, to determine the characteristic parameter, wherein an endoscope head has, or includes, a light exit area, or light output area, (e.g. a light exit surface or a light exit face) through which the endoscope lighting outputs a light amount of a light emitted from a light source, the light emitted from the light source having a luminosity or light output power up to a preset maximum luminosity. In other words, the light emitted by the endoscope lighting can be understood as an output light. This output light has a luminosity that, due to losses, is usually less than the preset maximum luminosity of the light source. This means that the output light can be understood as a portion, or fraction or part, i.e. a light amount (e.g. a light portion or light fraction), of the light emitted by the light source. The relation applies that a change in the luminosity of the output light may be caused by a change in the luminosity of the light source. If, for example, the luminosity of the light source is increased/decreased, then the luminosity of the output light, i.e. of the light amount, rises/falls.

The light that leaves the endoscope head, i.e. has passed through the light exit area of the endoscope head, is referred to as the light amount. The light exit area is formed by the optical element through which the light amount leaves the endoscope head. For example, the light exit area can be formed by an expanding (or expander) optics (e.g. an expanding lens), a light exit window (light output window) located in a cap, or cover, of the endoscope head, a light guide that guides the light from the light source to the endoscope head, or a light-emitting element, such as an LED, arranged in the endoscope head.

The characteristic parameter is based on the light amount that is incident on the light detection unit. The processing unit is adapted to readjust the preset maximum luminosity based on the determined characteristic parameter.

By means of the endoscope apparatus according to the present disclosure with the measuring device, it is possible to readjust a maximum luminosity, or maximum light output power, of a light source associated with an endoscope, in such a way that an associated luminosity of a light emitted at a distal end of the endoscope apparatus does not fall below a predetermined minimum luminosity, or minimum light output power. As a result, it is possible to avoid replacing elements in the endoscope apparatus that are affected by degradation, for example. Such degradation may include, for example, reduced luminosity of the light source, increasing losses when coupling light into a light-guiding element, a broken or hazy light-guiding element, a scratched or hazy expanding optics, or a scratched or hazy light exit window of a cap. The present disclosure thus allows savings in terms of time, materials and costs.

Furthermore, the light source can be integrated in the endoscope apparatus. Alternatively, the light source can be adapted to be connected to the endoscope apparatus.

The measuring device according to the present disclosure is therefore not limited to a specific type of light source, but is applicable to different types of light sources. Thus, it is conceivable, for example, that the measuring device is used for a light source the light of which is directed via light-guiding elements, for example optical fibers, to the distal end of the endoscope apparatus. The measuring device can also be used if the light source is formed, or embodied, as an internal light source, for example in the form of LEDs, in the endoscope head.

The processing unit may also be adapted to readjust the preset maximum luminosity such that a luminosity of the light amount is equal to or less than a predefined luminosity threshold.

The advantage of this is, among other things, that an insufficient luminosity of the light amount leaving the endoscope head, for example due to individual broken optical fibers in a fiber bundle or a scratched, contaminated (e.g. stained or dirty), or hazy, or clouded, light exit window, can be counteracted by appropriate readjustment, or adjustment, of the light source. Replacement of the entire fiber bundle can be prevented in these cases. In general, the measuring device according to the present disclosure allows for compensating losses in the light guiding in the endoscope system due to fiber breaks and/or fiber-connector losses when using optical fibers.

The endoscope lighting may have as the at least one optical element a light guide, adapted to guide the light of the light source to the endoscope head where the light amount is emitted from the light exit area.

For example, such a light guide may be represented by, or embodied as, at least one optical fiber, at least one fiber bundle of individual optical fibers, or another light-guiding element or medium. The measuring device according to the present disclosure can therefore be used for different types of endoscope apparatus.

In addition, the endoscope lighting may also have, or include, an expanding (or expander) optics (e.g. an expanding lens) and/or a light exit window as a further optical element, wherein the light exit area is formed by the expanding optics or, insofar as (i.e. in case or provided that) the endoscope lighting includes the light exit window as the further optical element, by the light exit window. The light exit window may be formed in a cap, or cover, that covers the distal end of the endoscope head.

In addition, the measuring device can be adapted so that the light amount emitted by the at least one optical element, for example, the light guide, and incident on the light detection unit illuminates a section on the light detection unit, wherein an area of the section is larger than or equal to the cross-sectional area of the at least one optical element. The light detection unit may also be adapted to measure a light-emitting area (i.e. an area that is emitting light) of the at least one optical element and to determine a ratio of the light-emitting area of the at least one optical element to a non-light-emitting area (i.e. an area that is not emitting light) of the at least one optical element (i.e. the light detection unit can, for example, measure the illuminated area of a light guide and express it as a ratio of/to a non-illuminated area of the light guide). This can be achieved or implemented, for example, by the light detection unit knowing a reference area defined in advance (for example, a size of a light-emitting area of an end portion of the light guide, if there is no degradation) over which the at least one optical element, for example the light guide, emits light.

It should further be noted that, if, for example, a light exit window is present, the measuring procedure described above can in principle also be applied to the light exit window. This means that a light-emitting (illuminated) area of the light exit window can be expressed as a ratio of/to a non-light-emitting (non-illuminated) area of the light exit window, or of/to an area of the light exit window that is less intensely light-emitting (less strongly illuminated) in relation to the total area of the light exit window. A less intensely light-emitting area is to be understood as an area from which the emitted light, for example, is below a certain predetermined brightness threshold and/or is, for example, by a certain percentage (10%, 20%, 30% or any other percentage not listed here) below an average brightness of the light emitted from the total area of the light exit window.

For example, if the light detection unit is made up of an arrangement of a plurality of pixels, the light amount being incident on the plurality of pixels in such a way allows for avoiding a collimation or focusing of the light such that a light-emitting area is greater than or equal to a light-receiving area. This reduces the risk of individual pixels being over-exposed. In other words, it reduces the risk that one or more of the plurality of pixels reach a saturation state or level in respect of converting the light incident on them into electrical charges before a predetermined period of time has elapsed.

The at least one optical element (for example, a light guide) may have a first optical element (a first light guide) and a second optical element (a second light guide), and the section of the light detection unit illuminated by the incident light amount may have a first section and a second section. In this case, the measuring device may be adapted such that a first part of the light amount emitted via the first optical element illuminates the first section of the light detection unit and a second part of the light amount emitted via the second optical element illuminates the second section of the light detection unit, the first and second sections not overlapping each other. In this case, it is advantageous if the light detection unit is embodied in the form of an imaging sensor system.

Such a configuration in principle offers the possibility to distinguish between the first and second optical element (the first and second light guide) based on the information detected through the first and second sections of the light detection unit. This means that in principle a possibility is provided to, based on the information obtained, for example, replace only one of two light guides and/or readjust the maximum preset luminosity for each of the two light guides individually.

Furthermore, the processing unit may be adapted to distinguish between the first optical element (for example, the first light guide) and the second optical element (for example, the second light guide), based on a distinction of characteristic parameters obtained from the first section and the second section, and to individually readjust the preset maximum luminosity for the first optical element (for example, the first light guide) and the second optical element (for example, the second light guide).

Based on the above-mentioned distinguishability of the first and second optical elements, this results, among other things, in the advantage as already shown that the readjustment of the preset maximum luminosity for, for example, the first and second optical element can be individually detected, evaluated, and implemented. If the degradation states of the two optical elements differ, the risks of overloading (e.g. overly straining or stressing), or incorrect loading (e.g. incorrectly straining or stressing), of one of the optical elements can thus be reduced.

In particular, the measuring device may also include a telecentric lens (e.g. a telecentric objective) that is arranged in such a way that the light amount, after passing through the light exit area, passes through the telecentric lens and is incident on the light detection unit, which is arranged in the measuring device.

By using the telescopic lens, the beam path of the light emitted from the endoscope head of the endoscope apparatus can be manipulated or modified. Thus it is possible to look perpendicularly through the telecentric lens at/onto the distal end of the endoscope apparatus, for example at/onto the light-emitting end of the at least one optical element, i.e. for example, the at least one optical fiber, or the at least one fiber bundle.

The light detection unit can also be an imaging sensor system that is also adapted to determine image data based on the light amount incident on the imaging sensor system as a characteristic parameter. In other words, in this case, the imaging sensor system can be embodied as, for example, a camera integrated in the measuring device, or an image sensor that generates image data based on the incident light and transmits it to an external device for further processing, for example wirelessly or by wire/cable. A display unit can be used to display an image that (as image information obtained, or derived, from the image data) shows, for example, a plan view of the plane that includes the plane of the light exit area. This means that if a light guide element, such as fiber bundles, is used, an image can show the light-emitting distal end portion of these fiber bundles. The image data can identify or represent among others, but not limited to, (maximum, minimum) light intensity values, or a light intensity distribution, (maximum, minimum) contrast values, or a contrast distribution (contrast, for example, between sections that emit light at different intensities and sections that do not emit light) and/or (maximum, minimum) brightness values, or a brightness distribution.

This in principle offers the possibility to evaluate the degradation state of the endoscope apparatus based on at least one image of the distal end of the endoscope apparatus in a light-emitting and/or non-light-emitting state (insofar as the measuring device provides a separate light source for illumination during the image acquisition).

Regardless of the actual implementation of the measuring device, the image information (i.e. information obtained from an image such as, for example, the above-mentioned image of the distal end portion of a fiber bundle and of a light-emitting area to be determined therefrom, the image having been generated on the basis of the image data obtained) can also include, based on the image data, at least one image of the end portion of the at least one optical element in a light-emitting state. The processing unit may also be adapted to, on the basis of the image information, derive a fraction of a light-emitting area of the end portion compared to a total area of the end portion, and/or, insofar as the endoscope apparatus includes a light guide as the at least one optical element and the light guide includes a plurality of optical fibers, to derive a degradation degree of the plurality of optical fibers (for example, brightness loss of 5%, 10% or 15% (or any other threshold not mentioned here) compared to a reference brightness value due to haze/contamination of the end portion), and/or to derive a number of defective and/or non-defective optical fibers of the plurality of optical fibers (number of defective, or broken optical fibers greater than a preset threshold of, for example, 10%, 15% or 20% (or any other threshold not mentioned here)). In concrete terms, for example, a ratio can be determined between a light-emitting area of the total area and the total area. For example, if the total area is determined by the distal end portions of a plurality of optical fibers, a ratio of 1 indicates that all optical fibers emit light. If the ratio falls below a value of 1, there are, conversely, optical fibers present that do not emit light and are broken, for example. The greater the ratio deviates from the ideal value 1, the larger the number of broken optical fibers can be estimated to be. If a predefined threshold is reached, for example a threshold of 0.7, 0.6 or 0.5 (or any other threshold not mentioned here), and if the preset maximum luminosity is already readjusted in such a way (for example, during the readjustment of the preset maximum luminosity a preset readjustment threshold of, for example, 120%, 130%, or 140% (or any other threshold not mentioned here) of the originally preset maximum luminosity is reached) that a further readjustment of the preset maximum luminosity cannot compensate for the condition or state of the optical fibers, or that a further readjustment of the preset maximum luminosity is not permitted, then the processing unit can issue, or output, a replacement of the affected optical fibers (of the affected fiber bundle) as an alternative action, or course of action.

Furthermore, the processing unit can be adapted to derive scratching and/or haze/hazing (e.g. cloudiness) and/or contamination of the light exit window. This means that the processing unit can also be adapted to derive an impairment (degradation) degree of the light exit window in the form of at least one of a contamination (e.g. dirt or stain), a scratch, or a haze, based on the image information. In this case, a violation (exceeding) of an impairment threshold can be estimated by a user (e.g. by visual inspection of the light exit window). Alternatively, an image of the light exit window (and/or of a light entrance window, or light entry window, for example, of an endoscope-head-internal camera) in its current state can be compared with a reference image or a plurality of reference images of the light exit window representing, for example, different states of degradation and the current degradation state of the light exit window can be derived using, for example, image processing methods or the user's estimation ability.

The measuring device according to the present disclosure thus enables individual potential degradation effects of a plurality of different potential degradation effects to be investigated in a targeted manner.

The processing unit can further be adapted to perform the readjustment of the preset maximum luminosity if the degradation degree exceeds a preset degradation degree threshold (a preset threshold of/for the degradation degree) and/or the number of defective optical fibers, if present, exceeds a preset number threshold (a preset threshold of/for said number of defective optical fibers).

In this way, exemplarily illustrated in the case of the use of fiber bundles of individual optical fibers, replacement of an entire fiber bundle made of individual optical fibers can be avoided. Instead, for example, if the preset threshold of the degradation degree and/or the preset threshold of said number (of defective optical fibers) is exceeded, a processing or treatment, for example cleaning or polishing, of the light-emitting ends of the optical fibers can be derived, or inferred, as an alternative action, or course of action, in order to reduce the determined degradation degree. Alternatively or in addition, the preset maximum luminosity can be readjusted to compensate for the degradation condition or state at the light-emitting ends of the optical fibers and/or for individual defective or broken optical fibers. If, for example, the optical fibers are affected by degradation to such an extent (for example, if a predetermined impairment degree as described below is reached) that the processing/treatment and/or readjustment cannot/should not compensate for the loss/luminosity loss resulting from the degradation, it may be necessary, for example, to replace the optical fibers.

Alternatively or in addition, the processing unit can also be adapted to prevent the readjusting of the preset maximum luminosity if the impairment degree of the light exit window exceeds a preset threshold of the impairment degree (a preset impairment degree threshold).

The information provided by the measuring device, according to the examples discussed above, offers the advantage of determining the degradation state of the endoscope apparatus for different elements of the endoscope apparatus and in different ways. In particular, the information collected allows an image-based evaluation (obtained image data for generating an image for obtaining image information). Alternatively, the measuring device can be configured to reflect the light amount emitted by the endoscope head back to the camera integrated in the endoscope head. In this case, the image data is obtained via the camera of the endoscope head and the image information is derived from the endoscope image generated by the endoscope apparatus. At the same time, the camera could also detect contaminations (e.g. stains or dirt), scratches and haze of/affecting the light exit area (and/or, for example, the lens surface (expanding optics/lens)), given an appropriate choice of aperture. This requires a camera with sufficient depth of field to detect the consecutive layers of fiber bundles (if present) and the lens surface.

A degradation, or reduction of the luminosity of the light amount can then be detected statistically over time, for example from the sum of all pixel intensities (i.e. individual pixel values) correlated with the respective values of the brightness control (exposure time, gain). In addition, the image-based evaluation of the image dynamics (for example, the contrast) allows conclusions to be drawn about the contamination and/or haze of/affecting the camera window and/or the light exit window.

The readjusting of the preset maximum luminosity can be prevented or discontinued/not be carried out further for various reasons. In simple terms, an existing degradation state/degradation degree of the endoscope apparatus and/or of an element of the endoscope lighting, for example of the at least one optical element, may have progressed to such an extent that (further) readjusting the preset maximum luminosity will not be able to compensate for this advanced degradation state or the loss/luminosity loss resulting therefrom.

In addition, the measuring device can be mountable on the endoscope head of the endoscope apparatus and also include an Ulbricht sphere (integrating sphere) with a diffusely reflecting inner surface, which is adapted to diffusely reflect the light amount before it impinges on, or reaches, the light detection unit. The light detection unit in this case is a photosensor.

The implementation of the measuring device in conjunction with an Ulbricht sphere offers an option that is technically simple to implement. Furthermore, it should be noted that the implementation in conjunction with the Ulbricht sphere can also be used in the case of a light guide as the at least one optical element which has, for example, a first light guide and a second light guide.

The measuring device can also be mountable on an endoscope head of the endoscope apparatus and include a diffuser which is adapted to opaquely diffuse the light amount before it impinges on, or reaches, the light detection unit. The light detection unit in this case is a photosensor.

The implementation of the measuring device in conjunction with a diffuser also offers an option that is technically simple to implement. Furthermore, it should be noted that the implementation in conjunction with the diffuser can also be used in the case of a light guide as the at least one optical element, which has, for example, a first light guide and a second light guide.

In addition, the measuring device can also include a dark field light detection unit, which is adapted to determine a dark field characteristic parameter (e.g. dark field characteristic value or dark field characteristic quantity or property) that corresponds to a dark field light amount of the light amount. In this case, light is emitted at, for example, the distal end portion of a light guide element or an LED in the endoscope head and passes through a light exit window (which defines the light exit area), which is preferably formed in the cap of the endoscope head. The light behind the light exit window (behind the light exit area), i.e. the light that has passed through the light exit window, is referred to as the light amount, as already discussed above. For example, due to haze, a scratch or a contamination, some of the light is scattered when passing through the light exit window, i.e. the original beam path is changed. In a simple view, the light amount can therefore be understood as having two components, on the one hand light with an (almost) unchanged beam path (no scattering at the light exit window) and on the other, light scattered at the light exit window. The dark field light detection unit is arranged in the measuring device in such a way that the light with the (almost) unchanged beam path does not impinge, or is not incident, on the dark field light detection unit. However, the dark field light detection unit is arranged in the measuring device in such a way that the scattered light, or a part of the scattered light, impinges, or is incident, on the dark field light detection unit. This light, which impinges on the dark field light detection unit, is called the dark field light amount of the light amount.

Thus, the dark field light amount is scattered at the light exit area of the light exit window and impinges on the dark field light detection unit. The dark field light detection unit is arranged in the dark field of the light exit window, as described above. Furthermore, in this case the processing unit is adapted to, at least based on the determined characteristic parameter or the determined dark field characteristic parameter, readjust at least the preset maximum luminosity and/or output information on a reflectance of the light exit window.

The use of a dark field light detection unit allows additional information about the potential degradation state of the endoscope apparatus to be obtained. In particular, the state/condition and influence of the light exit window can be assessed. The evaluation and handling of a possible degradation can therefore be additionally specified.

Furthermore, the processing unit can also be adapted to prevent the readjusting of the preset maximum luminosity if the reflectance exceeds a predetermined threshold of the reflectance (a predetermined reflectance threshold).

This means, as already discussed above, that an existing degradation state of the endoscope apparatus and/or of an element of the endoscope lighting may have progressed to such an extent that a readjusting of the preset maximum luminosity cannot compensate for a loss/luminosity loss resulting from this advanced degradation state.

This adaptation of the processing unit has the advantage that the preset maximum luminosity does not need to be readjusted if, for example, replacing or polishing/cleaning the light exit window (and/or alternatively the light entrance window, or light entry window, of the camera) is considered beneficial for reducing the detected reflectance and thus for reducing the luminosity losses present. An additional demand on, or usage of, the light source and the at least one optical element, for example the optical fibers, due to a readjusting of the preset maximum luminosity can thus be avoided.

The light detection unit can also be adapted to determine a plurality of characteristic parameters at different points in time. In this case, the processing unit is further adapted to derive degradation information based on the plurality of characteristic parameters and to readjust the preset maximum luminosity based on the degradation information.

In this way, a statistical evaluation can be further specified, for example, taking into account a temporal variation of potential luminosity losses.

Furthermore, the light detection unit can also be adapted to determine a plurality of dark field characteristic parameters at different points in time. In this case, the processing unit is further adapted to derive dark field degradation information based on the plurality of dark field characteristic parameters and to readjust the preset maximum luminosity based on the dark field degradation information.

In this way, a statistical evaluation can be additionally specified.

Furthermore, the processing unit can also be adapted to terminate the readjusting and/or determine to at least replace the at least one optical element, the light exit area, or the light source when the readjusting of the preset maximum luminosity reaches a replacement indication state.

In this way, an alternative action, or course of action, can be determined, the implementation of which can make it possible to eliminate the degradation that has occurred, even if compensation can/should no longer be realized, or achieved, by readjusting the preset maximum luminosity.

In addition, the replacement indication state can be associated with preventing or discontinuing the readjusting of the preset maximum luminosity, as mentioned above. This means that a degradation state of the endoscope apparatus and/or of an element of the endoscope lighting, such as the at least one optical element, may have reached a replacement indication state, for example, if a degradation degree that is present has progressed to such an extent that a (further) readjustment of the preset maximum luminosity cannot/should not compensate for the resulting loss/luminosity loss (see also the impairment degree threshold, reflectance threshold presented above). Reaching the replacement indication state can lead to termination of the readjusting and/or to determination of, among others, alternative actions, or courses of action, presented below.

Such a replacement indication state can be reached, for example, if the preset maximum luminosity has already been readjusted up to a predetermined maximum readjustment luminosity (so that continuing the readjustment can lead to damage to the light source of the endoscope apparatus or the illuminant of the light source). Alternatively, or in addition, such a replacement indication state may be reached, for example, when (as already discussed above) a number of degraded optical fibers, for example broken optical fibers, of a fiber bundle reaches a predetermined (fiber bundle) impairment degree threshold and/or when contaminations, scratches and/or haze of/affecting the light exit area (for example, light exit window or expanding optics) and/or a lens surface (for example, of the expanding optics) reach a predetermined impairment degree threshold and/or reflectance threshold, from which on the readjusting of the preset maximum luminosity is prevented or discontinued. Instead of or in addition to this, the processing unit can determine a recommendation/alternative action, or course of action, which may possibly be replacing the affected element(s) of the endoscope apparatus and/or the endoscope lighting (where possible). For each such element, for example the optical fibers of a fiber bundle, the light exit area, a lens surface and/or an expanding optics, predetermined impairment degree thresholds may be used to determine, for example, whether to continue the readjusting. For example, a predetermined impairment degree threshold may be a number or quantity of non-light-emitting optical fibers, for example broken optical fibers, such as at least 70%, 80%, or 90% (or any other threshold not mentioned here). This means that if, for example, 70% or more of the optical fibers are broken, the readjusting of the preset maximum luminosity is prevented or discontinued. In the case of contaminations, scratches and/or haze of/affecting the light exit area, a lens surface and/or an expanding optics, a predetermined impairment degree threshold can be defined, for example, based on already degraded and/or prepared reference elements. An existing impairment degree threshold can be determined by a comparison with such a reference element. In addition, an existing impairment degree threshold can be understood as the characteristic parameter determined by the measuring device.

The processing unit can therefore be configured to make a decision as to whether the readjustment of the preset maximum luminosity will be carried out or continued, or whether the readjustment will be prevented or discontinued. The processing unit (as already mentioned) may also be adapted to determine alternative actions, or courses of action, if the processing unit makes the decision to prevent the readjustment. For example, the alternative action, or course of action, can be replacing a fiber bundle, replacing a light exit area, a lens surface and/or an expanding optics, or replacing the light source or an illuminant of the light source of the endoscope apparatus. As already mentioned, an alternative action, or course of action, can be determined when a predetermined impairment degree threshold is reached. In relation to the light source or to an illuminant of the light source, reaching a predetermined deviation from a predetermined reference luminosity may lead to a recommendation to replace the light source or the light source illuminant.

DETAILED DESCRIPTION OF EXAMPLES

A measuring device for detecting a light output power, or luminosity, at the distal end of an endoscope apparatus can be used to maintain an originally set light output power when the light output power is degraded, on condition that no thermal limits are exceeded at the distal end of the endoscope apparatus in respect of the risk to a subject that is to be examined (for example, a patient's body cavity that is to be examined). This is possible by readjusting or correcting a light source (which may be formed, or embodied, as an internal or external light source) associated with the endoscope apparatus that generates the light emitted at the distal end of the endoscope apparatus, based on a characteristic parameter (e.g. characteristic value or characteristic quantity or property) corresponding to the degradation degree.

Possible types of degradation that is to be expected with respect to the endoscope apparatus include, among others, a decreasing power of the light source and haze/hazing (e.g. cloudiness) or contamination (e.g. dirt or stains/staining) of optical elements such as, for example, light guiding elements, e.g. optical fibers, of an expanding optics (e.g. an expanding lens) that is present and/or a light exit window (light output window) that is present (and/or a light entrance window (light entry window) that is present in the case of an endoscope-head-internal camera). Fiber breaks must also be taken into account when using optical fibers.

In this context, examples of the present disclosure are described in detail below with reference to the figures.

Figure 1:
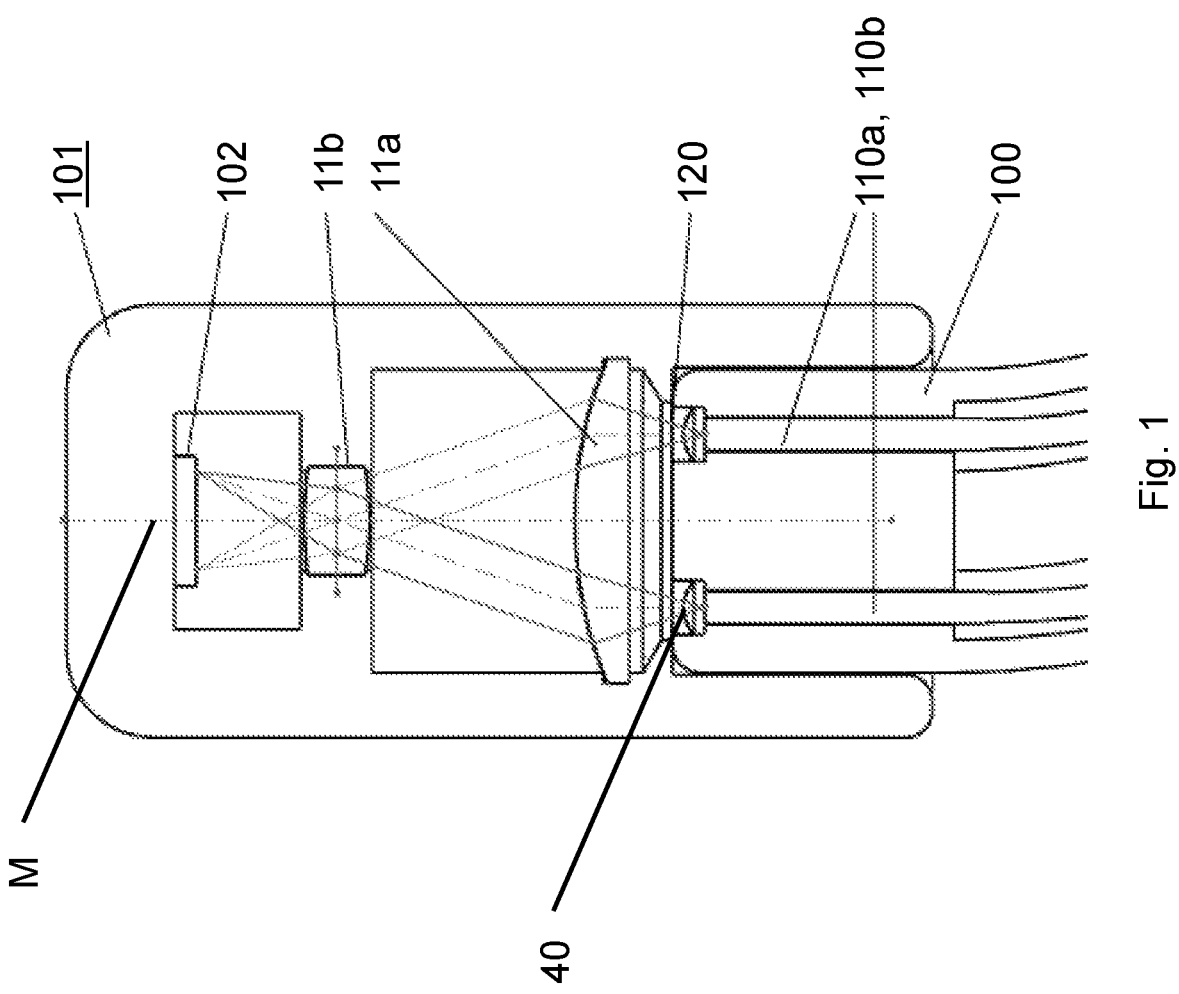
FIG. 1 schematically illustrates an endoscope head with a mountable measuring device according to a first example of the present disclosure.

FIG. 1 schematically illustrates an endoscope head 100 with a measuring device 101 which can be mounted, for example, put or plugged on, according to a first example of the present disclosure.

In particular, FIG. 1 shows the mountable measuring device 101, which includes a telecentric lens (telecentric objective) 11a, 11b and a light detection unit 102.

In the present example, the telescopic lens, which includes two lenses 11a and 11b, is arranged in such a way that, after the measuring device 101 has been mounted on the endoscope head 100, a central axis M of the first lens 11a in the direction of propagation of the light amount (amount, e.g. part or fraction, of light generated by a light source (not shown) that is transmitted via light guides 110a, 110b, which are used in this example as the at least one optical element, and emitted, or output, at the distal end portions thereof in the endoscope head 100 and has passed through the expanding (or expander) optics (e.g. expanding lens) 40 and the light exit window (light output window) 120, which are used as further optical elements in this example, and is emitted, or output, behind the light exit window that defines a light exit area (light output area)), a central axis M of the second lens 11b in the direction of propagation of the light amount, and a central axis M of the endoscope head 100 in the direction of propagation of the light amount coincide (lie on top of one another). The two lenses 11a and 11b each have a first side on which light impinges, or is incident, and a second side through which light leaves the respective lens. The first and second sides are located on opposite sides of the associated lens. The first sides are each facing towards the endoscope head 100. The light amount impinges, or is incident, on the first side of the first lens 11a, exits through the second side of the first lens 11a (taking losses into account where applicable), impinges on the first side of the second lens 11b, exits through the second side of the second lens 11b (taking losses into account where applicable), and impinges on the light detection unit 102.

The endoscope head 100 in this example includes two light guides made up of optical fibers (two fiber bundles of individual optical fibers) 110a, 110b, which, via a respective expanding (or expander) optics (e.g. an expanding lens) 40 provided in a recess of the endoscope head 100, output light that is generated by a light source (not shown) and guided onward via the light guides 110a, 110b, through an associated light exit window 120 defining a light exit area, the light exit window 120 being part of a cap, or cover, (not shown) of the endoscope head 100, from the light exit area at the distal end of the endoscope apparatus. However, the use of the measuring device 101 is not restricted to the use of optical fibers or fiber bundles. According to a modification of the present example, the optical fibers or fiber bundles, for example, can be generally represented by, or embodied as, a light-guiding element or medium, or can each be replaced by, for example, an endoscope-head-internal light source such as an LED, or by an arrangement of a plurality of endoscope-head-internal light sources.

As mentioned above, the light exit windows 120 can be integrated in a cap that can be plugged or fitted onto the endoscope head 100. The cap is to be understood as an attachment, top or cover that can be plugged or fitted onto the endoscope head 100 and includes light exit windows 120 (or light entrance windows) at positions where light is emitted from the endoscope head 100 (light enters the endoscope head 100, for example, for the endoscope-head-internal camera). The light exit windows 120 each form a light exit area (light output area). The light emitted through the light exit area (the emitted light amount) has a luminosity, or light output power, which due to losses occurring in the light guiding is less than a maximum luminosity that is emitted by a light source (not shown) at the proximal end of the endoscope apparatus at the light guides 110a, 110b and passed, or coupled, into the light guides 110a, 110b. The light emitted from the light exit area at the distal end of the endoscope apparatus, for the purposes of differentiation of terms, is referred to in the following as the light amount (light fraction or light portion) of the light emitted by the light source of the endoscope apparatus, wherein the light emitted by the light source of the endoscope apparatus has a luminosity which can usually be adjusted up to the preset maximum luminosity. In this case, the preset maximum luminosity of the light source of the endoscope apparatus should be readjusted to compensate for luminosity losses, for example due to degradation, in such a way that the luminosity of the light amount does not fall below a predetermined minimum luminosity.

The telecentric lens, which includes the two lenses 11a and 11b, is arranged in such a way that the light amount passes through the lenses 11a and 11b and impinges, or is incident, on the light detection unit 102. In the present example, the light detection unit 102 is an imaging sensor system. However, the light detection unit 102 is not limited to an imaging sensor system, but in a modification of the present example can be a photosensor, for example.

In FIG. 1, the imaging sensor system (light detection unit 102) is adapted to determine image data based on the incident light amount as a characteristic parameter. The image data can indicate among others, but not limited to, (maximum, minimum) light intensity values, or a light intensity distribution, (maximum, minimum) contrast values, or a contrast distribution (contrast, for example, between sections that emit light at different intensities and sections that do not emit light) and/or (maximum, minimum) brightness values, or a brightness distribution. In addition, the imaging sensor system allows image information to be obtained, for example based on the image data, as the characteristic parameter from a generated or acquired image (or a plurality of such images) of the distal end portion of the endoscope head 100 and/or the light exit windows 120, including the expanding optics 40 located behind the latter and the light guide 110a (110b) behind that.

It should be noted here that the light emitted by the light guides 110a, 110b in the example in accordance with FIG. 1 shown here is collimated or focused on a few pixels of the imaging sensor system (of the light detection unit 102). As a result, only a portion/fraction of all pixels is illuminated and it is possible to obtain data that can be used for evaluation. A degradation, or reduction, in the luminosity of the light amount emitted from the light exit area can then be detected statistically over time, for example from the sum of all pixel intensities (i.e. individual pixel values) correlated with the respective values of the brightness control (exposure time, gain). In addition, the image-based evaluation of the image dynamics (for example, the contrast) allows conclusions to be drawn about the contamination and/or haze of/affecting the light exit window 120. An appropriate brightness control to avoid overexposure of these few pixels should be considered.

In particular, FIG. 1 shows the possibility that the light guide 110*a*, 110*b* includes a first light guide 110*a* and a second light guide 110*b*, and a section of the imaging sensor system 102 illuminated by the incident light amount includes a first section and a second section, wherein a first part of the light amount emitted via the first light guide 110*a* (attributable to the first light guide 110*a*) illuminates the first section of the imaging sensor system 102 and a second part of the light amount emitted via the second light guide 110*b* (attributable to the second light guide 110*b*) illuminates the second section of the imaging sensor system 102. The first and second sections of the imaging sensor system 102 do not overlap each other. However, the imaging sensor system 102 is not limited to the structure shown in FIG. 1 and can be formed or embodied, for example, by two separate imaging sensors (one corresponding to the first section and one corresponding to the second section).

A processing unit (not shown) is adapted to readjust the preset maximum luminosity based on the determined characteristic parameter, in the present example based on generated image data. The structure shown in FIG. 1 allows characteristic parameters or image data to be obtained individually for the first light guide 110*a* and the second light guide 110*b*, thus enabling a distinction or individual readjusting. For example, an individual brightness value can be compared to a pre-determined reference brightness value (for example, percentage deviation of the individual brightness value from the reference brightness value). The reference brightness value can be a brightness value that has been determined for light guides (generally for optical elements used in the endoscope head) without any degradation effects.

In general, the structure shown in FIG. 1, for example, allows at least one image of the end portion of the light guides 110*a*, 110*b* in a light-emitting state to be obtained, for example on the basis of the image data. If the image shows the end portion of the light guides 110*a*, 110*b* in a light-emitting state, a light-emitting area of the end portion as a ratio of the total area of the end portion can for example be determined from this as image information (in this example to be considered as a characteristic parameter) of a comparison with an image (for example a reference image) of the end portion in a non-light-emitting state. The more the ratio determined from this deviates from the ideal value of 1, the greater the probability that, for example, individual optical fibers are affected by degradation and thus are broken, for example.

Figure 2:
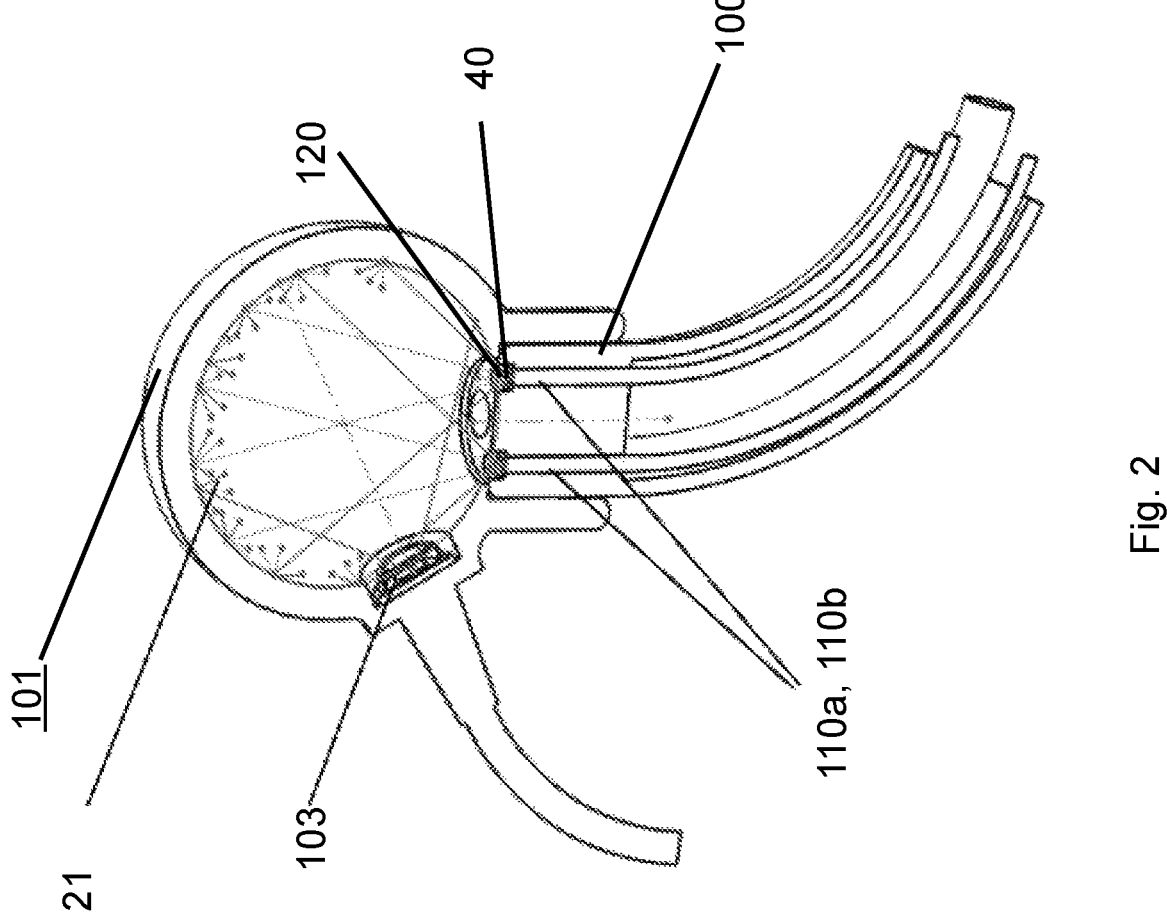
FIG. 2 schematically illustrates an endoscope head with an Ulbricht sphere as the mountable measuring device according to a second example of the present disclosure.

FIG. 2 schematically illustrates an endoscope head 100 with an Ulbricht sphere (integrating sphere) as the mountable measuring device 101 according to a second example of the present disclosure.

In particular, the structure shown in FIG. 2 differs from the structure shown in FIG. 1 in that FIG. 2 shows the use of an Ulbricht sphere as the mountable measuring device 101, wherein the Ulbricht sphere has a diffusely reflecting inner surface 21 which is adapted to reflect the light amount diffusely before it impinges, or is incident, on the light detection unit 103, which is embodied as or formed by a photosensor. The photosensor can be adapted to determine the result of a luminous flux measurement as the characteristic parameter. If, for example, a certain luminous flux is determined as the characteristic parameter, degradation information can be obtained based on a temporal change and/or a comparison with a (or a plurality of) pre-determined reference luminous flux value(s). The reference luminous flux value can be determined in such a way that it indicates the luminous flux that is to be expected for light guides (generally for optical elements used in the endoscope head) without degradation effects.

Figure 3:
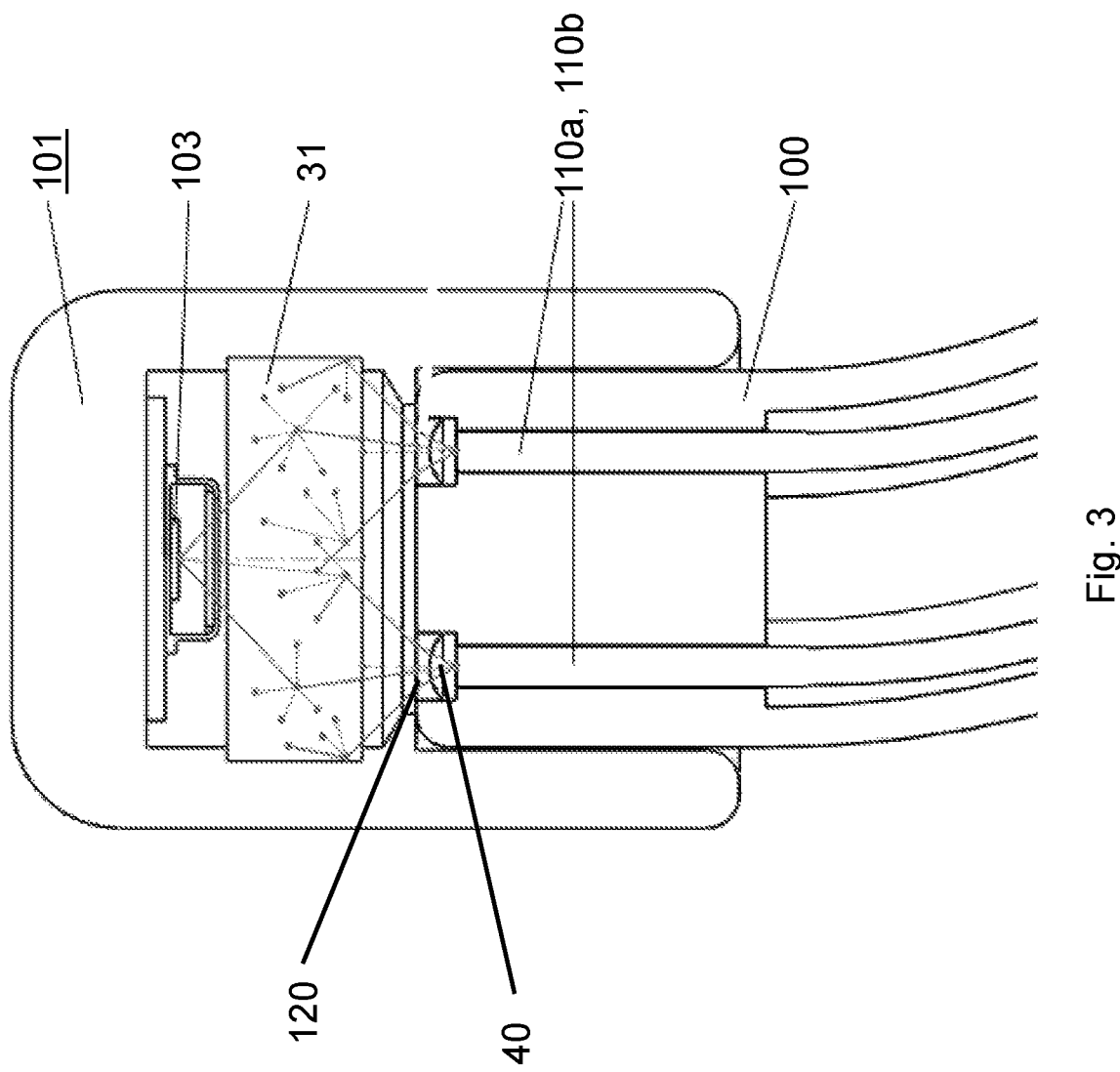
FIG. 3 schematically illustrates an endoscope head with a mountable measuring device according to a third example of the present disclosure.

FIG. 3 schematically illustrates an endoscope head 100 with a mountable measuring device 101 according to a third example of the present disclosure.

In particular, the structure shown in FIG. 3 differs from the structure shown in FIG. 1 in that FIG. 3 does not have a telecentric lens but rather a diffuser 31, and as the light detection unit 103, instead of an imaging sensor system it has a photosensor, analogous to the example with the Ulbricht sphere according to FIG. 2. The photosensor measures a luminous flux that is present analogous to the example shown in FIG. 2.

Figure 4:
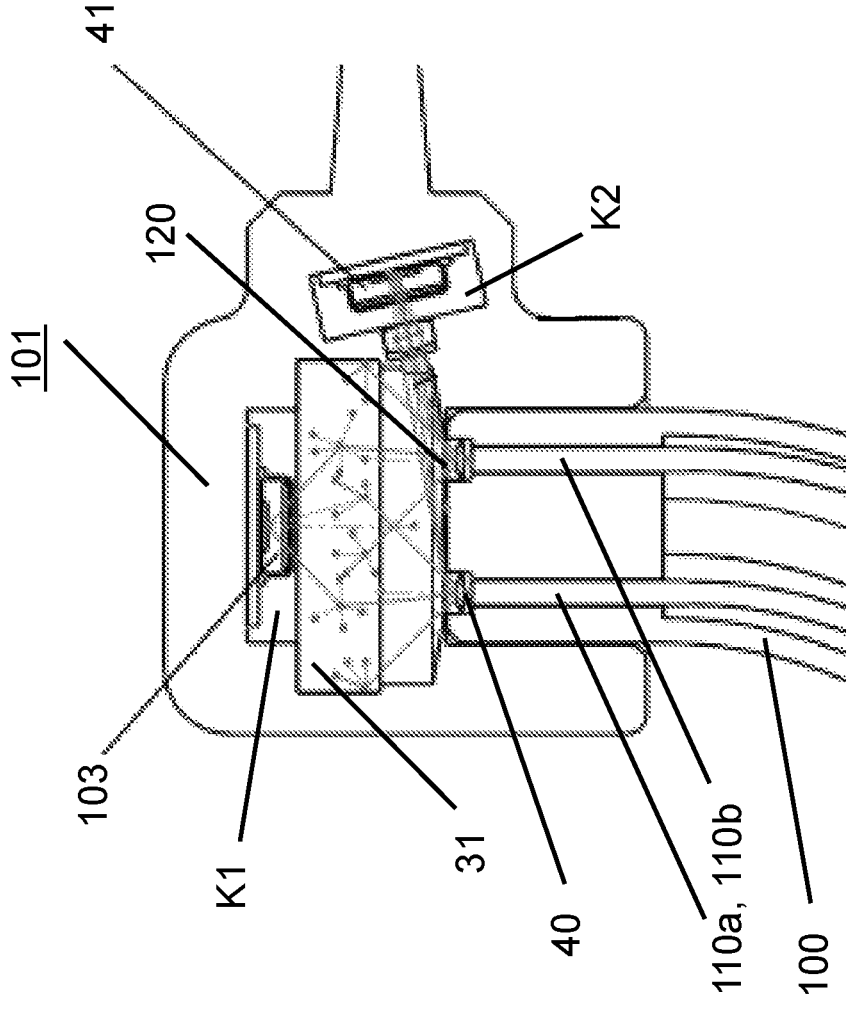
FIG. 4 schematically illustrates an endoscope head with a mountable measuring device according to a fourth example of the present disclosure.

FIG. 4 schematically illustrates an endoscope head 100 with a mountable measuring device 101 according to a fourth example of the present disclosure. In particular, the structure shown in FIG. 4 differs from the structure shown in FIG. 3 in that the structure shown in FIG. 4 also includes a dark field light detection unit 41. The dark field light detection unit 41 in the example shown here is a photosensor and can be adapted to determine the result of a dark field luminous flux measurement as a characteristic parameter.

Due to, for example, haze, scratches or contamination, part of the light emitted by the light guides 110*a* and 110*b* in the present example, after passing through the expanding optics 40, is scattered when passing through the light exit window 120, i.e. the original beam path is changed. The dark field light detection unit 41 is provided in the measuring device 101 (provided in the dark field of the light exit window 120) in such a way that light with an (almost) unchanged beam path does not impinge on the dark field light detection unit 41, but light scattered at the light exit window 120 does impinge on it. Furthermore, the dark field light detection unit 41 is provided in the measuring device 101 in such a way that light also scattered, or diffused, by the diffuser 31 does not impinge on the dark field light detection unit 41. The measuring device 101 can have two chambers K1 and K2, as shown in FIG. 4. The first chamber K1 is bounded on one side by the endoscope head 100 mounted to the measuring device 101 and includes the diffuser 31 and the photosensor (light detection unit 103). The second chamber K2 is connected to the first chamber K1 via a linear, or straight, channel and includes the dark field light detection unit 41. The channel is oriented in such a way that a first of the two openings of the channel faces the dark field light detection unit 41 and a second of the two openings of the channel faces the light exit window 120, with the second opening of the channel being arranged between the light exit window 120 and the diffuser 31.

A measured dark field luminous flux can, for example, provide information about a degree of contamination, scratching or haze/hazing of the light exit window 120, for example. Similar to the reference comparisons described above, a comparison (e.g. a percentage deviation) with a pre-determined reference dark field luminous flux value is possible. The reference dark field luminous flux value can be determined in such a way that it indicates the luminous flux that is to be expected for a light exit window 120 without any degradation effects.

Similarly, the dark field light detection unit 41 can also in principle be used to evaluate a degradation degree of the expanding optics 40.

The invention claimed is:

1. An endoscope apparatus comprising:
a measuring device adapted to be mountable on an endoscope head of the endoscope apparatus for determining a characteristic parameter of an endoscope lighting of the endoscope apparatus,
wherein the endoscope lighting comprises at least one optical element through which light passes, and
wherein the measuring device comprises a light detector adapted to determine the characteristic parameter, wherein
the endoscope head comprises a light exit area through which the endoscope lighting outputs a light amount of a light emitted from a light source, the light emitted from the light source having a luminosity up to a preset maximum luminosity, and
the characteristic parameter is based on a light amount incident on the light detector; and
a processor adapted to readjust the preset maximum luminosity based on the determined characteristic parameter, wherein
a light amount emitted from the at least one optical element and incident on the light detector illuminates a section on the light detector, and
an area of the section is larger than or equal to a cross-sectional area of the at least one optical element, and
the light detector is further adapted to measure a light emitting area of the at least one optical element and to determine a ratio of the light-emitting area of the at least one optical element to a non-light-emitting area of the at least one optical element.

2. The endoscope apparatus according to claim 1, wherein the light source
is integrated in the endoscope apparatus or
is adapted to be connected to the endoscope apparatus.

3. The endoscope apparatus according to claim 1, wherein the processor is further adapted to readjust the preset maximum luminosity such that a luminosity of the light amount of the light emitted from the light source is equal to or less than a predefined luminosity threshold.

4. The endoscope apparatus according to claim 1, wherein the endoscope lighting comprises a light guide as the at least one optical element, the light guide being adapted to guide the light of the light source to the endoscope head where the light amount is emitted from the light exit area.

5. The endoscope apparatus according to claim 4, wherein the endoscope lighting comprises an expanding optics and/or a light exit window as a further optical element, the light exit area being formed by the expanding optics or, insofar as the endoscope lighting comprises the light exit window as the further optical element, the light exit window.

6. The endoscope apparatus according to claim 1, wherein the light detector is an imaging sensor system, and
the at least one optical element comprises a first optical element and a second optical element, and the section of the light detector illuminated by the incident light amount comprises a first section and a second section, wherein a first part of the light amount emitted via the first optical element illuminates the first section of the light detector and a second part of the light amount emitted via the second optical element illuminates the second section of the light detector, the first and second sections not overlapping each other.

7. The endoscope apparatus according to claim 6, wherein the processor is further adapted to
distinguish between the first optical element and the second optical element based on a distinction of characteristic parameters obtained from the first section and the second section, and
individually readjust the preset maximum luminosity for the first optical element and the second optical element.

8. The endoscope apparatus according to claim 1, wherein the measuring device further comprises a telecentric lens arranged such that the light amount of the light emitted from the light source, after passing through the light exit area, passes through the telecentric lens and is incident on the light detector which is arranged in the measuring device.

9. The endoscope apparatus according to claim 8, wherein the light detector is an imaging sensor system that is further adapted to determine image data based on the light amount incident on the imaging sensor system as a characteristic parameter.

10. The endoscope apparatus according to claim 9, wherein
the imaging sensor system captures at least one image of an end portion of the at least one optical element in a light-emitting state, and,
the processor is further adapted to derive, based on the at least one image, as image information
a fraction of a light-emitting area of the end portion compared to a total area of the end portion, and/or
insofar as the endoscope apparatus comprises a light guide as the at least one optical element, the light guide being adapted to guide the light of the light source to the endoscope head where a light amount is emitted from the light exit area, and the light guide comprises a plurality of optical fibers,
a degradation degree of the plurality of optical fibers, and/or
a number of defective and/or non-defective optical fibers of the plurality of optical fibers, and/or,
insofar as the light exit area is covered with a light exit window,
the processor is further adapted to derive, based on the at least one image, as image information,
an impairment degree of the light exit window in the form of at least one of a contamination, a scratch, or a haze.

11. The endoscope apparatus according to claim 10, wherein
the processor is further adapted to perform the readjusting of the preset maximum luminosity if
the degradation degree exceeds a preset threshold of the degradation degree, and/or
insofar as the endoscope apparatus comprises a light guide as the at least one optical element, the light guide being adapted to guide the light of the light source to the endoscope head where the light amount is emitted from the light exit area, and the light guide comprises a plurality of optical fibers, the number of defective optical fibers exceeds a preset threshold of said number.

12. The endoscope apparatus according to claim 10, wherein, the processor is further adapted to prevent the readjusting of the preset maximum luminosity if the impairment degree of the light exit window exceeds a preset threshold of the impairment degree.

13. The endoscope apparatus according to claim 1, wherein the measuring device further comprises an Ulbricht sphere having a diffusely reflecting inner surface, which is adapted to diffusely reflect a light amount before impinging on the light detector, the light detector being a photosensor.

14. The endoscope apparatus according to claim 1, wherein the measuring device further comprises a diffuser adapted to opaquely diffuse the light amount before impinging on the light detector, the light detector being a photosensor.

15. The endoscope apparatus according to claim 14, wherein the measuring device further comprises a dark field light detector adapted to determine a dark field characteristic parameter that corresponds to a dark field light amount of the light amount of the light emitted from the light source, wherein the dark field light amount is diffused at a light exit window covering the light exit area and impinges on the dark field light detector, wherein the dark field light detector is arranged in the dark field of the light exit window, and the processor is further adapted to, at least based on the determined characteristic parameter or the determined dark field characteristic parameter, at least readjust the preset maximum luminosity or output information on a reflectance of the light exit window.

16. The endoscope apparatus according to claim 15, wherein the processor is further adapted to prevent the readjusting of the preset maximum luminosity if the reflectance exceeds a predetermined threshold of the reflectance.

17. The endoscope apparatus according to claim 1, wherein the light detector is further adapted to determine a plurality of characteristic parameters at different points in time, and the processor is further adapted to derive degradation information based on the plurality of characteristic parameters and to readjust the preset maximum luminosity based on the degradation information.

18. The endoscope apparatus according to claim 15, wherein the light detector is further adapted to determine a plurality of dark field characteristic parameters at different points in time, and the processor is further adapted to derive dark field degradation information based on the plurality of dark field characteristic parameters and to readjust the preset maximum luminosity based on the dark field degradation information.

19. The endoscope apparatus according to claim 1, wherein the processor is further adapted to terminate the readjusting and/or determine to at least replace the at least one optical element, the light exit area or the light source when the readjusting of the preset maximum luminosity reaches a replacement indication state.

\* \* \* \* \*